United States Patent [19]
Cseh

[11] Patent Number: 4,676,978
[45] Date of Patent: Jun. 30, 1987

[54] SHAMPOO

[75] Inventor: Edomer G. Cseh, Koge, Denmark

[73] Assignee: Colgate-Palmolive Company, New York, N.Y.

[21] Appl. No.: 822,445

[22] Filed: Jan. 27, 1986

Related U.S. Application Data

[63] Continuation of Ser. No. 542,630, Oct. 17, 1983, abandoned.

[51] Int. Cl.$^4$ .................. A61K 7/06; A61K 31/74; C11D 3/48; C11D 9/50
[52] U.S. Cl. .................. 424/70; 252/106; 252/107; 424/DIG. 4; 424/78
[58] Field of Search .................. 424/70

[56] References Cited

U.S. PATENT DOCUMENTS

| | | | |
|---|---|---|---|
| 3,816,616 | 6/1974 | Angiullo et al. | 424/70 |
| 3,849,548 | 11/1974 | Grand | 424/70 |
| 3,987,162 | 10/1976 | Scheuermann | 424/70 |
| 4,292,212 | 9/1981 | Melby et al. | 424/70 |
| 4,315,912 | 2/1982 | Kalopissis et al. | 424/70 |
| 4,364,837 | 12/1982 | Pader | 424/70 |
| 4,397,322 | 8/1983 | Arbaczawski | 424/70 |

FOREIGN PATENT DOCUMENTS

| | | | |
|---|---|---|---|
| 0027730 | 4/1981 | European Pat. Off. | 424/70 |
| 0024799 | 3/1981 | Fed. Rep. of Germany | 424/70 |
| 3032216 | 4/1982 | Fed. Rep. of Germany | 424/70 |
| 0072095 | 6/1981 | Japan | 424/70 |
| 1333475 | 10/1973 | United Kingdom | 424/70 |
| 2091102 | 7/1982 | United Kingdom | 424/70 |

OTHER PUBLICATIONS

Garlen, Cosmetics & Toiletries, 3/1979, pp. 66 to 68.

Primary Examiner—Dale R. Ore
Attorney, Agent, or Firm—Richard N. Miller; Richard J. Ancel; Herbert S. Sylvester

[57] ABSTRACT

A hair-conditioning shampoo based on anionic washing-active substances and containing from 0.1 to 4% by weight of a polycationic guar derivative, from 0.5% to 5% by weight of a hardenable cationic polycondensation product, from 1 to 4% by weight of a hydrophilic fatty acid ester and from 0.1 to 1.0% by weight of a polyvinyl pyrrolidone gives particularly good wet-combability values and improves the hair-cosmetic properties of hair after drying.

8 Claims, No Drawings

SHAMPOO

This is a continuation of application Ser. No. 542,630 filed Oct. 17, 1983, now abandoned.

This invention relates to hair-conditioning shampoos and body-washing preparations.

After washing with shampoos, shower and bath preparations based on synthetic anionic surfactants, the hair often is in a cosmetically unsatisfactory state. When wet, it is difficult to comb and feels dull. After drying, the washed hair tends to develop a static charge, resulting in the well-known "flying away" of freshly washed hair. In addition, freshly washed hair often appears lustreless. For these reasons, it is known that conditioning preparations may be applied to hair after washing or shampooing. The preparations in question are mostly rinses or cream-like lotions containing cation-active surfactants. It is also known that certain substances may be added to ordinary shampoos to obtain a certain conditioning effect when the hair is washed. Substances of the type in question include, for example, water-soluble proteins or protein degradation products, polycationic polymers, for example amino polycarbamide resins of the type described in DE-OS No. 21 50 899, polycationic cellulose derivatives of the type described in U.S. Pat. No. 3,816,616 or polycationic guar derivatives of the type described in U.S. Pat. No. 4,292,212. Many other water-soluble polymers containing cationic or quaternary ammonium groups have been proposed for this purpose.

One disadvantage common to all known hair-conditioning additives lies in their at least partly reduced effect when used in anion-active hair washing preparations. Products having a particularly strong effect often show excessive adsorption to the hair and, as a result, reduce the elasticity, body and set of the dried hair.

Accordingly, the object of the present invention is to provide a shampoo formulation based on the well-known, heavily foaming anionic washing-active substances which, through the presence of suitable hair-reviving additives, enables the hair to be readily combed when wet and also leaves the dry hair with satisfactory cosmetic properties, including in particular elasticity, body, sheen and set.

It has now been found that the hair-care properties of a shampoo based on anionic washing-active substances may be improved particularly effectively by adding to the shampoo a combination of a polycationic quar derivative, a hardenable cationic polycondensation product, a hydrophilic fatty acid ester and a water-soluble polyvinyl pyrrolidone. Accordingly, the present invention relates to a hair-conditioning shampoo based on an aqueous solution of anionic washing-active substances and standard set-up agents which is characterized by a content of from 0.1 to 4% by weight of 3-(trimethylamino)-2-hydroxy propyl guar chloride,
from 0.5 to 5% by weight of a readily water-soluble, hardenable polycondensation product of water-soluble polyamines containing reactive amino groups and polyalkylene oxide radicals with epichlorohydrin or compounds containing more than one epoxide group and/or halohydrin group in the molecule,
from 1 to 4% by weight of an esterification product of ethylene oxide adducts of glycerol and 4 to 20 moles of ethylene oxide with 1 to 2 moles of a $C_8$–$C_{18}$ fatty acid,
from 0.1 to 1% by weight of a polyvinyl pyrrolidone having an average molecular weight of at least 10,000.

The 3-(trimethylamino)-2-hydroxy propyl guar chloride is a cationic guar derivative known from U.S. Pat. No. 3,589,978. The products described therein contain as their basic unit two mannose units attached by a glucosidic bond and one galactose unit attached to one of the hydroxyl groups of the mannose units. On average, each of the hexose rings carries three free hydroxyl groups. These free hydroxyl groups are reacted with reactive quaternary ammonium compounds to give the cationic polymers. The cationic polymer used in the shampoo according to the invention is commercially available under the name "Cosmedia ® Guar C 261."

The readily water-soluble, hardenable, polycondensation products of water-soluble polyamines containing reactive amino groups and polyalkylene oxide radicals with epichlorohydrin or compounds containing more than one epoxide and/or halohydrin group in the molecule are known from DE-PS No. 2,363,871. As set forth in said patent, to prepare the hardenable polycondensation products to be employed in the invented compositions, it is necessary to proceed from polyamines with a content of polyalkylene oxide radicals, which are obtained via known procedure by reacting polyamines, especially polyalkylene polyamines with mono- and/or polyfunctional derivatives of polyalkylene oxides. These mono- and/or polyfunctional derivatives of polyalkylene oxides can contain, as reactable groups, chlorohydrin radicals, glycidyl radicals, halogen or other radicals capable of anion formation such as, for example, sulfuric acid radicals, alkylsulfuric acid radicals, alkylsulfonic acid radicals and so forth. The polyalkylene oxide groups present in the polyalkylene oxide derivatives can have varying molecule sizes, in which case the starting material is generally so chosen that approximately from 3 to 70 alkylene oxide radicals are available. As an alkylene oxide, ethylene oxide is the first to come under consideration; but other cyclic oxides such as, for example, propylene oxide, as well as corresponding mixtures, are also usable. The polyalkylene oxide chains can also be interrupted, for example, via the insertion of a dicarboxylic acid or diisocyanate radical.

Compounds usable as a second reaction component include those containing in the molecule more than one epoxide and/or halogen hydrin group, such as epichlorohydrin, dichlorohydrins or bifunctional reaction products of these compounds with glycols, diglycols, polyalkylene oxides, glycerin, dicarboxylic acids, multivalent phenols, etc.

The preparation of certain hardenable polycondensation products to be employed in the inventive compositions can be effected via an especially simple procedure by reacting a polyalkylene glycol, e.g., a poly-oxyethylene glycol having a molecular weight of 1000 or 600, with epichlorohydrin to form a bis chlorohydrin ether and by then further reacting this product with sufficient polyamine, e.g., dipropylene triamine, diethylene triamine or triethylene tetraamine, to produce in the reaction mixture a ratio of available chlorine atoms to available amino hydrocarbon atoms in the range of from 4:5 to 7:5. In this production process, the intermediately formed polyglycol polyamine is not isolated, but is immediately reacted with additional polyglycol bis chlorohydrin ether to form the desired polycondensation product. The reaction of the polyamines, which contain polyalkylene oxide radicals, with those compounds containing in the molecule more than one epoxide and/or halogen hydrin group, can be carried out in the presence of organic solvents or, preferably, of water. To speed up the reaction, appropriate acid-binding substances, such as caustic alkali, sodium carbonate, magnesium carbonate or triethanolamine can also be included.

The reaction is carried out at temperatures between 50° and 100° C. for a period of time sufficiently long to produce a clear increase in the viscosity of the reaction product. The reaction is terminated as soon as the desired degree of polycondensation—at which point the reaction product is still readily soluble—has been achieved, if necessary by means of adjusting the pH to <6.

Of the cationic polycondensation products described in German DE OS No. 2,363,871 the polycondensate produced as product F of the above-mentioned patent is particularly suitable for use in the production of the hair-conditioning shampoos according to the invention.

PRODUCT F

Placed into a heatable and coolable agitator vessel, equipped with a reflux cooler and a thermometer, are 180 kg. of liquid polyglycol 600. At a temperature of approximately 30° C. and with agitation, 2.7 kg. of tin tetrachloride are slowly added to the same. After raising the heat to 68°-78°, 56 kg. of epichlorohydrin are added with steady stirring and possible cooling so quickly that the temperature of the mixture remains between 68° and 70°. Agitation is continued for an hour at temperatures of approximately 70°. The total quantity of the obtained crude polyglycol-bis-chlorohydrin ether amounts to 239 kg.

80 kg. of the obtained crude chlorohydrin ether are placed in a second agitator vessel with a capacity of approximately 600 liters, capable of heating and cooling and equipped with a thermometer and reflux cooler, and combined in the presence of agitation with 13.2 kg. of dipropylene triamine, 50 kg. of water and 28 kg. of caustic soda solution. The vessel is then heated for 45 minutes to the boiling point, with reflux cooling. The quantity of crude chlorohydrin ether of the polyglycol 600 remaining in the first vessel is then added with the application of agitation and kept at boiling for an additional 20-30 minutes after the addition of a further 30 kg. of water. The pH of the viscous reaction product is reduced during this time to about 7.2. Vigorous cooling is then applied. The pH is adjusted during cooling to 5.5-6 via the addition of approximately 38 kg. of 10% aqueous hydrochloric acid solution. The yield is about 400 kg. of a slightly yellowish, slightly opaque and highly viscous liquid.

One product of this type is commercially available for example under the name of Polyquart H ®.

The esterification products of ethylene oxide adducts of glycerol and 4 to 20 moles of ethylene oxide with 1 to 2 moles of a $C_8$-$C_{18}$ fatty acid are known from DE-AS No. 20 24 051. Of the esterification products mentioned therein, a partial ester obtained by the addition of 7.4 moles of ethylene oxide with 1 mole of glycerol, followed by the esterification of 1 mole of the resulting adduct with 1 mole of $C_8$-$C_{18}$ coconut oil fatty acid, is particularly suitable for use in the hair-conditioning shampoos according to the invention. A product having this composition is commercially available for example under the namde of Cetiol HE ®. Polyvinyl pyrrolidones having an average molecular weight of approximately 40,000, corresponding to a K-value of approximately 30, are particularly suitable for the production of the hair-conditioning shampoos according to the invention.

The concentration of the above mentioned mixture of essential conditioning agents in the final shampoo may range from 1.7-14% by weight, and a range from 2-8% by weight is preferred.

The ratio of the various essential conditioning agents mentioned above may vary. Generally, the ratio will be about 1 part of the guar derivative to 0,5-4 parts of Polyquart ®H to 0,5-4 parts of Cetiol ®HE to 0,15-0,5 parts of PVP.

The hair-conditioning shampoos according to the invention preferably contain as water-soluble anionic washing-active substances alkali metal, magnesium, ammonium and/or $C_2$-$C_3$ alkanolammonium salts of alkyl sulfuric acid semiesters containing from 8 to 18 and preferably from 12 to 16 carbon atoms in the alkyl radical or of alkyl polyglycol ether sulfuric acid semiesters containing from 8 to 18 and preferably from 12 to 16 carbon atoms in the alkyl radical and from 1 to 6 glycol ether groups in the molecule. Other suitable anionic washing-active substances are primary and secondary linear alkane sulfonates containing from 10 to 18 carbon atoms, alkene sulfonates and hydroxy alkane sulfonates of the type obtained in the sulfonation of olefins containing from 10 to 18 carbon atoms, $C_8$-$C_{18}$ fatty acid alkylol amide polyglycol ether sulfates, $C_8$-$C_{18}$ fatty acid monoglyceride sulfates, sulfosuccinic acid monoalkyl esters containing from 8 to 18 carbon atoms in the alkyl group or dialkyl esters containing from 6 to 18 carbon atoms in the alkyl groups, alkyl polyglycol ether carboxylates containing from 8 to 18 carbon atoms in the alkyl group and 2 to 6 polyglycol ether groups in the molecule and acyl sarcosines, acyl taurides and acyl isethionates containing from 8 to 18 carbon atoms in the acyl group.

In general, the concentration of anionic surfactants in the shampoo may range from about 5 to about 50% by weight; a preferred range is about 8 to about 30% by weight.

A preferred anionic surfactant comprises a mixture of sodium lauryl polyglycol ether sulfate and fatty alcohol sulfate in a ratio of about 2:1 to 1:1 by weight. The fatty alcohol sulfate preferably contains an alcohol moiety with about 10-14 C-atoms, preferably 12-14 C atoms. The ratio of the total amount of anionic surfactants present to the mixture of essential conditioning agents may vary from about 10:1 to 1:1, preferably from 2,5:1 to 1,5:1.

In addition, the hair-conditioning shampoos according to the invention may contain standard additives and set-up agents, such as for example thickeners of the $C_8$-$C_{18}$ fatty acid alkylolamide type, opacifiers, for example of the ethylene glycol distearate type, pH-stabilisers, such as alkali or ammonium phosphates or citrates, preservatives, such as formaldehyde or p-hydroxy benzoic acid esters, dyes, fragrances and known hair-cosmetic active substances, such as anti-dandruff agents or sebostatics.

The hair-conditioning shampoos having the composition according to the invention are distinguished by an unexpectedly marked improvement in the hair-conditioning properties of hair washed with them. For example, the so-called wet combability of the hair conditioning shampoos according to the invention is considerably improved in relation to shampoos containing only one of the conditioning components, e.g. Cosmedia Guar®C 261. This is the more surprising as the other essential ingredients have little or no influence on wet-combability themselves. Similar surprising synergistic effects can be observed if the parameters sheen, feel, and antistatic properties, the so-called "conditioning effect", are investigated.

Also the feel (elasticity) and sheen of the dry hair are improved by the shampoos according to the invention to a greater extent than with conventional shampoos containing for example only one of the components required in accordance with the invention. Finally, the tendency of the hair to develop an electrostatic charge after drying is considerably reduced by using the conditioning shampoo according to the invention. The hair tends less to "fly away", can be combed more easily and retains its shape for longer periods.

The hair-cosmetic effects obtained with a hair conditioning shampoo according to the invention are shown in the following examples by comparison with conventional shampoos.

EXAMPLES

Shampoo formulations according to the invention (nos. 1-3) are comparatively tested with analogous shampoo formulations containing none (No. 10) or only part (Nos. 4 to 9) of the necessary components of the shampoos according to the invention.

The performance-tested shampoo formulations are set out in Table 1.

EXAMPLE 1

Determination of wet-combability (laboratory test)

Wet-combability was determined by measuring the resistance to combing, i.e., the force required to draw a comb through a tuft of hair. A modified tensile testing machine (type 1402 as manufactured by the Zwick Company of Einsingen uber Ulm/Danube) was used. The test arrangement is described in "Riechstoffe, Aromen, Kosmetika, No. 12/1977", page 325, columns 2 and 3.

Standardized strands of hair which had been predamaged by bleaching and permanent-waving under defined conditions were used. They were washed with the shampoos set out in Table 1 in hand-warm water and rinsed with clear water.

In order to minimize error, the resistance to combing was determined 15 times with each of the shampoos to be tested and the average values calculated. The average combing resistance values are quoted in percent of the blank value. The blank value was determined after shampooing with an aqueous solution containing 10% by weight of sodium lauryl ether diethenoxy sulfate and rinsing with clear water.

TABLE 1

|  | 1 | 2 | 3 | 4 | 5 | 6 | 7 | 8 | 9 | 10 |
|---|---|---|---|---|---|---|---|---|---|---|
| Fatty alcohol ($C_{12/14}$)-poly (2EO)glycol ether sulfate, sodium salt | 5.5 | 10 | 5.5 | 5.5 | 5.5 | 5.5 | 5.5 | 5.5 | 5.5 | 5.5 |
| Fatty alcohol ($C_{12/14}$)sulfate, monoethanol ammonium salt | 4.5 | — | 4.5 | 4.5 | 4.5 | 4.5 | 4.5 | 4.5 | 4.5 | 4.5 |
| Ethylene glycol distearate (20% dispersion in alkyl ether sulfate solution) | 3.0 | 3.0 | 3.0 | 3.0 | 3.0 | 3.0 | 3.0 | 3.0 | 3.0 | 3.0 |
| Cosmedia guar C 261 ®* | 2.0 | 2.0 | 0.8 | — | — | 1.5 | — | 1.2 | — | — |
| Polyquart H 81 ®** | 1.0 | 3.0 | 2.5 | — | 2.5 | — | — | — | 2.0 | — |
| Cetiol HE ®*** | 1.5 | 1.0 | 2.5 | 1.5 | — | — | — | 2.0 | 2.0 | — |
| Luviskol K 30 ®**** | 0.6 | 0.6 | 0.4 | — | — | — | 0.5 | 0.6 | 0.6 | — |
| Perfume oil | 0.8 | 0.8 | 0.8 | 0.8 | 0.8 | 0.8 | 0.8 | 0.8 | 0.8 | 0.8 |
| Preservative (Bronidox L5 ®) | 0.4 | 0.4 | 0.4 | 0.4 | 0.4 | 0.4 | 0.4 | 0.4 | 0.4 | 0.4 |
| Citric acid | 0.2 | 0.2 | 0.2 | 0.2 | 0.2 | 0.2 | 0.2 | 0.2 | 0.2 | 0.2 |
| Water | 78.5 | 79.0 | 79.4 | 83.6 | 83.6 | 84.4 | 85.0 | 81.8 | 81.0 | 85.6 |
| Resistance to wet combing in % of the value obtained after washing with a sodium lauryl ether sulfate solution | 26% | 25% | 27% | 95% | 70% | 35% | 110% | 31% | 75% | 100% |

*Guar-hydroxypropyl-trimethylammonium chloride (CTFA name is Guar Hydroxypropyl trimmonium chloride)
**Polyglycol polyamine condensation resin
***Polyethylene glycol (7.5) glyceryl monococate
****Polyvinyl pyrrolidone having an average molecular weight of 40,000

EXAMPLE 2

Testing of hair-cosmetic properties (salon test)

The testing and assessment of the hair-cosmetic properties were carried out on 10 test subjects differing from one another in the quality of their hair using the so-called half-side test. The test was carried out by a trained hairdresser. The half-side test is used for the comparative testing of two hair treatment preparations or one hair treatment preparation and one standard on test subjects. In the present tests, hair shampoo No. 1 according to the invention was used as the standard. The comparison marks given in Table 2 are a measure of the extent to which hair shampoos Nos. 4 to 10 differ from the assessment of shampoo No. 1.

Procedure and evaluation

The hair of the test subjects was wetted and parted in the middle. The standard shampoo was applied to the left-hand half of the heads of 5 of the test subjects and the comparison shampoo to the right-hand half in equal quantities of 5 g in each case (pre-wash). In the case of the other 5 test subjects, the other half of their heads was treated with the same product. Both sides were shampooed in the same way and rinsed with water. For the main wash, the shampoos were applied once again to the same half of the head in quantities of 2.5 g, rubbed in to form a lather and thoroughly rinsed out with clear water.

During and after washing, the criteria set out in Table 2 below were separately assessed by the hairdresser for each of the two sides. Assessment was carried out by the awarding of marks (1 = excellent, 2 = good, 3 = moderate, 4 = poor). From the marks awarded for the 10 test subjects, the average values were calculated for the same product. The average values for the standard product were subtracted from the average values for the comparison product. The pair difference thus obtained in the average values of the assessments of 10 test subjects is shown in Table 2 below.

Result: The comparison shampoos were all judged to be poorer in their hair-cosmetic properties than the standard shampoo (shampoo No. 1 according to the invention).

TABLE 2

| Salon tests | Comparison with shampoo No. 1 (pair difference) | | | | | | | |
|---|---|---|---|---|---|---|---|---|
| | 1 | 4 | 5 | 6 | 7 | 8 | 9 | 10 |
| Wet hair | | | | | | | | |
| Combability | ±0 | −1.2 | −0.6 | −0.4 | −1.0 | −0.4 | −0.6 | −1.2 |
| Feel | ±0 | −0.9 | −0.8 | −0.3 | −0.8 | −0.5 | −0.8 | −0.8 |
| Dry hair | | | | | | | | |
| Antistatic | ±0 | −0.5 | −0.3 | −0.5 | −0.6 | −0.1 | −0.3 | −0.6 |
| Feel (elasticity) | ±0 | −0.5 | −0.4 | −0.6 | −0.3 | −0.5 | −0.3 | −0.6 |
| Sheen | ±0 | −0.5 | −0.3 | −0.2 | −0.5 | −0.4 | ±0 | −0.5 |

What is claimed is:

1. A hair conditioning shampoo consisting essentially of 5 to 50% by weight of a water soluble, anionic, alkali metal, magnesium, ammonium or $C_2$–$C_3$ alkanol ammonium detergent salt selected from the group consisting of $C_8$–$C_{18}$ alkyl sulfates, $C_8$–$C_{18}$ alkyl polyglycol ether sulfates having 1 to 6 glycol ether groups in the molecule, $C_{10}$–$C_{18}$ alkane sulfonates, $C_{10}$–$C_{18}$ olefin sulfonates, $C_8$–$C_{18}$ fatty acid alkylolamide polyglycol ether sulfates, $C_8$–$C_{18}$ fatty acid monoglyceride sulfates, $C_8$–$C_{18}$ alkyl sulfosuccinates, $C_6$–$C_{10}$ dialkylsulfosuccinates, $C_8$–$C_{18}$ alkyl polyglycol ether carboxylates having 2-6 polyglycol ether groups in the molcule, $C_8$–$C_{18}$ acyl sarcosinates, $C_8$–$C_{18}$ acyl taurides and $C_8$–$C_{18}$ acyl isethionates and 1.7% to 14% by weight of a mixture of conditioning agents consisting of (1) 0.1% to 4% by weight of 3 (trimethylamino)-2-hydroxypropyl guar chloride, (2) 0.5% to 5% by weight of a readily water-soluble, hardenable polycondensation product formed by reacting a water-soluble polyamine containing reactive amino groups and having from 4 to 6 carbon atoms with an ether of poly $C_2$–$C_3$ alkylene glycol having terminal halohydrin or hydroxyl groups followed by reaction with either epichlorohydrin or the addition reaction product of said polyamine and said ether, (3) 1% to 4% by weight of an esterification product formed by reacting 1 to 2 moles of $C_8$–$C_{18}$ fatty acid with the adduct obtained by reacting 4 to 20 moles of ethylene oxide with 1 mole of glycerol and (4) 0.1% to 1% by weight of a polyvinyl pyrrolidone having an average molecular weight of 10,000 to 70,000, the weight ratio of (1):(2):(3):(4) being 1:0.5–4:0.5–4:0.15–0.5 and the weight ratio of said anionic detergent to said conditioning mixture being from 10:1 to 1:1 in an aqueous medium.

2. A shampoo according to claim 1 wherein 2% to 8% by weight of said conditioning mixture is present.

3. A shampoo according to claim 2 wherein said anionic detergent is present in an amount of 8% to 30% by weight.

4. A shampoo according to claim 3 wherein the weight ratio of said detergent to said mixture is from 2.5:1 to 1.5:1.

5. A shampoo according to claim 1 wherein said anionic detergent is a mixture of said $C_8$–$C_{18}$ alkyl polyglycol ether sulfate and $C_8$–$C_{18}$ alkyl sulfate in a ratio of 2:1 to 1:1 by weight.

6. A shampoo according to claim 2 wherein said anionic detergent is a mixture of said $C_8$–$C_{18}$ alkyl polyglycol ether sulfate and $C_8$–$C_{18}$ alkyl sulfate in a ratio of 2:1 to 1:1 by weight.

7. A shampoo according to claim 3 wherein said anionic detergent is a mixture of said $C_8$–$C_{18}$ alkyl polyglycol ether sulfate and $C_8$–$C_{18}$ alkyl sulfate in a ratio of 2:1 to 1:1 by weight.

8. A shampoo according to claim 4 wherein said anionic detergent is a mixture of said $C_8$–$C_{18}$ alkyl polyglycol ether sulfate and $C_8$–$C_{18}$ alkyl sulfate in a ratio of 2:1 to 1:1 by weight.

* * * * *